United States Patent [19]
Peng et al.

[11] Patent Number: 5,877,300
[45] Date of Patent: Mar. 2, 1999

[54] PREPARATION OF GUANIDINIUM 5'5-AZOTETRAZOLATE

[75] Inventors: Yu-Lin Peng; Chi-Wung Wong, both of Taoyuan, Taiwan

[73] Assignee: Chung Shan Institute of Science & Technology, Taoyuan, Taiwan

[21] Appl. No.: 99,943

[22] Filed: Jun. 19, 1998

[51] Int. Cl.$^6$ ............... C07D 257/06; C07C 279/02
[52] U.S. Cl. .............................................. 534/765
[58] Field of Search ............................... 534/765

[56] References Cited

FOREIGN PATENT DOCUMENTS 4034645  5/1992  Germany .

*Primary Examiner*—Patricia L. Morris
*Attorney, Agent, or Firm*—Bacon & Thomas, PLLC

[57] ABSTRACT

A process for the preparation of a guanidinium 5,5'-azotetrazolate by reacting 5-aminotetrazolate monohydrate with potassium permanganate in an aqueous hydroxide solution to form sodium 5,5'-azotetrazolate dihydrate as an intermediate, then reacting 5,5'-azotetrazolate dihydrate with guanidine nitrate or guanidine chloride to obtain guanidinium 5,5'-azotetrazolate.

4 Claims, No Drawings

PREPARATION OF GUANIDINIUM 5'5-AZOTETRAZOLATE

BACKGROUND OF THE INVENTION

The present invention relates to the preparation of guanidinium 5,5'-azotetrazolate (GZT).

Various sodium azide ($NaN_3$) based materials are known for generating gas on combustion. However, there are some problems in using sodium azide, such as high toxicity and high water-solubility. Therefore, much effort has been concentrated on the development of the non-$NaN_3$ gas generating compounds.

Germany patent No. 4,034,645 disclosed a gas generating compound, guanidinium 5,5'-azotetrazolate, molecular formula $C_4H_{12}N_{16}$, molecular weight 284.5, with a very high nitrogen content up to 78.8%. Guanidinium 5,5'-azotetrazolate is a very stable salt and insoluble in common organic solvents except for methanol, DMF, and DMSO. It is sparingly soluble in water and exhibits high thermal stability, as can be seen from its high melting point of 238°–239° C. The particular advantage for the application of this compound is that the generated gas and reaction by-products of combustion are harmless to human beings. This is particularly important when it is used in a closed space.

The manufacturing process described in the Germany patent No. 4,034,645 includes first dissolving 5-aminotetrazole monohydrate in 15% aqueous NaOH solution, then adding powdered $KMnO_4$ to form sodium 5,5'-azotetrazolate pentahydrate as an intermediate in 51% yield, and followed by reacting with guanidine nitrate to form the final product in 84% yield.

SUMMARY OF THE INVENTION

It is therefore an object of the present invention to provide an improved method for the preparation of guanidinium 5,5'-azotetrazolate that can provide an increased production yield by varying the reaction conditions.

Another object of the present invention is to provide an improved method that can reduce the production cost via the formation of a different intermediate during the preparation of guanidinium 5,5'-azotetrazolate.

Thus, within the present invention is a process for the preparation of guanidinium 5,5'-azotetrazolate which comprises the steps of:

(a) dissolving 5-aminotetrazolate monohydrate in aqueous sodium hydroxide solution;

(b) adding aqueous potassium permanganate solution;

(c) refluxing the resulting solution to obtain sodium 5,5'-azotetrazolate dihydrate; and (d) reacting said sodium 5,5'-azotetrazolate dihydrate with guanidine nitrate or guanidine chloride to obtain guanidinium 5,5'-azotetrazolate. In this method, 5-aminotetrazolate monohydrate is oxidized by potassium permanganate ($KMnO_4$) in an alkaline solution to form sodium 5,5'-azotetrazolate dihydrate as an intermediate.

Both of guanidine nitrate and guanidinium chloride are commercially available and inexpensive reagents.

DESCRIPTION OF THE PREFERRED EMBODIMENTS

The reaction mechanism of the present invention can be described as below.

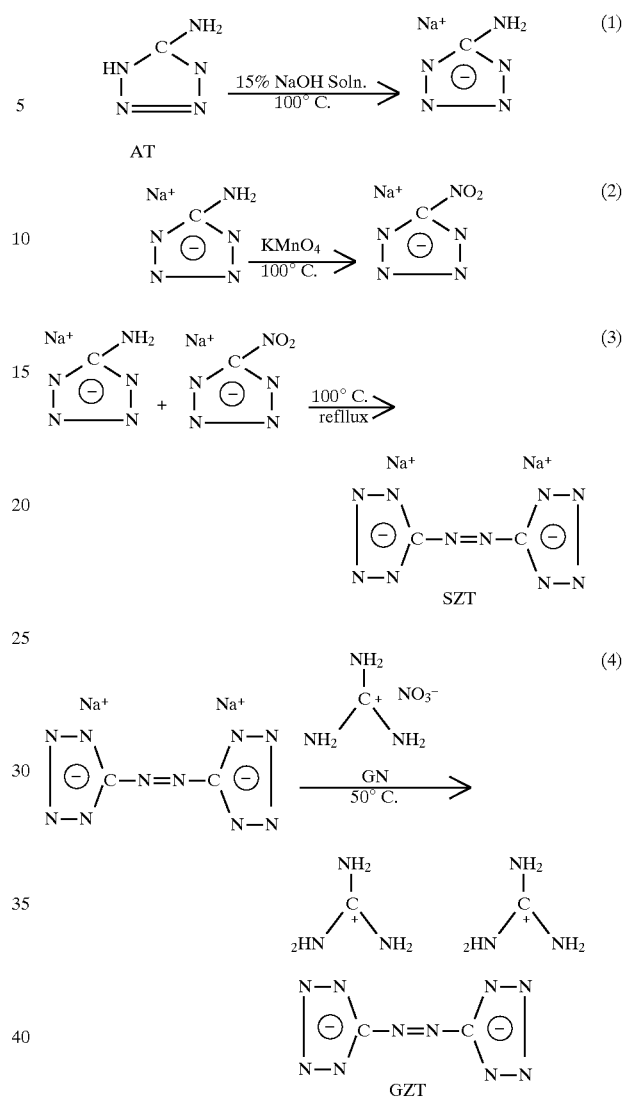

By comparing the synthetic process in the present invention with that disclosed in the Germany patent No. 4,034,645, the present invention has the following differences or advantages: (1) The intermediate in present invention is sodium 5,5'-azotetrazolate dihydrate; but the intermediate in the Germany Pat. No. 4,034,645 is sodium 5,5'-azotetrazolate pentahydrate. (2) In the present invention, the dosage of NaOH can be reduced by about 40%, and the amount of $KMnO_4$ used can be reduced by about 23%. The yield in the first stage was increased by 21%, the yield in the second stage was increased by 5%, and thus, the total yield was increased by 22%. (3) $KMnO_4$ was fed as a solution instead of powder form. The feeding can be smoothly controlled, and sudden and violent bumping of the reaction solution can be avoided.

The present invention will be fully understood from the following examples.

EXAMPLE 1

Ten grams of 5-aminotetrazolate monohydrate was dissolved in 40 ml of 15% aqueous sodium hydroxide solution. The mixture was stirred and heated at 50° C. Another solution of 10 g of potassium permanganate in 50 ml of hot water was prepared. The aqueous $KMnO_4$ solution was added with stirring to the aqueous NaOH solution of 5-aminotetrazolate monohydrate, and 10 ml of ethanol was added to react with excess $KMnO_4$. Then, the mixed solution was refluxed at 100° C. for 1 hour. The resulting reaction solution was then filtered. After cooling, yellow crystals of sodium 5,5'-azotetrazolate dihydrate (SZT) crystallized from the filtrate. After recrystallization, the purified product was dried and weighed. The yield in this first stage was 63.3%.

Three grams of SZT was dissolved in 60 ml of distilled water. Another solution of 3.6 g guanidine nitrate in 20 ml of distilled water was prepared. These two solutions were heated and then mixed with stirring. Yellow needles of GZT started to crystallize and next day these needle crystals were filtered, recrystallized, dried, and weighed. The yield in this second stage was 88.4%.

ANAL. Calcd. C 16.9% H 4.26% N 78.8% Found C 16.9% H 4.26% N 78.8%

EXAMPLE 2

5-Aminotetrazolate monohydrate (10 g) was dissolved with stirring in 40 ml of 15% aqueous NaOH solution at 50° C. Another solution of 10 g of $KMnO_4$ in 50 ml of hot distilled water was prepared. The aqueous $KMnO_4$ solution was then added slowly into the stirred aqueous NaOH solution of 5-aminotetrazolate monohydrate. Into this mixture 10 ml of ethanol was added to react with excess $KMnO_4$. Then, the reaction solution was refluxed at 100° C. for 1 h. The resulting reaction mixture was then filtered. Upon cooling, yellow crystals of sodium 5,5'-azotetralate dihydrate (SZT) crystallized from the filtrate gradually. The crude product was recrystallized and dried to give 9.13 g (76.4%) of pure SZT.

SZT (3 g) was dissolved in 60 ml of distilled water, and another solution of guanidine nitrate dissolved in 20 mL of distilled water was prepared. The solutions were heated individually and mixed to react at 50° C. for 10 min. Yellow needle crystals of GZT crystallized gradually, which was filtered, recrystallized, dried, and weighed. The yield was 3.21 g (92.7%).

ANAL. Calcd. C 16.9% H 4.26% N 78.8% Found C 17.0% H 4.20% N 79.5%

From the foregoing description, one skilled in the art can easily ascertain the essential characteristics of this invention, and with departing from the spirit and scope thereof, can make various changes and modifications of the invention to adapt it to various usages and conditions. Thus, other embodiments are also within the claims.

What is claimed is:

1. A process for preparing guanidinium 5,5'-azotetrazolate comprising the steps of:
    (a) dissolving 5-aminotetrazolate monohydrate in aqueous sodium hydroxide solution;
    (b) adding aqueous potassium permanganate solution;
    (c) refluxing the resulting solution to obtain sodium 5,5'-azotetrazolate dihydrate; and
    (d) reacting said sodium 5,5'-azotetrazolate dihydrate with guanidine nitrate or guanidine chloride to obtain guanidinium 5,5'-azotetrazolate.

2. The process of claim 1, wherein said 5,5'-azotetrazolate dihydrate of the step (d) is reacted with guanidine nitrate to obtain guanidinium 5,5'-azotetrazolate.

3. The process of claim 1, wherein said step (b) is further added ethanol to react with excess potassium permanganate.

4. The process of claim 1, wherein said step (a) is performed by heating and stirring.

* * * * *